(12) United States Patent
Nau, Jr.

(10) Patent No.: US 8,114,122 B2
(45) Date of Patent: Feb. 14, 2012

(54) APPARATUS, SYSTEM, AND METHOD FOR PERFORMING AN ELECTROSURGICAL PROCEDURE

(75) Inventor: William H. Nau, Jr., Longmont, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 505 days.

(21) Appl. No.: 12/352,942

(22) Filed: Jan. 13, 2009

(65) Prior Publication Data

US 2010/0179539 A1 Jul. 15, 2010

(51) Int. Cl.
*A61B 17/00* (2006.01)
*A61B 18/18* (2006.01)

(52) U.S. Cl. .................. 606/207; 606/50; 606/206

(58) Field of Classification Search .......... 606/205–213, 606/50–51, 45
See application file for complete search history.

(56) References Cited

U.S. PATENT DOCUMENTS

| | | | |
|---|---|---|---|
| 5,405,344 A | | 4/1995 | Williamson et al. |
| 5,454,823 A | | 10/1995 | Richardson et al. |
| 5,472,442 A | | 12/1995 | Klicek |
| 5,496,347 A | | 3/1996 | Hashiguchi et al. |
| 5,575,799 A | | 11/1996 | Bolanos et al. |
| 5,626,607 A | | 5/1997 | Malecki |
| 5,690,653 A | | 11/1997 | Richardson et al. |
| 5,720,742 A | * | 2/1998 | Zacharias .......................... 606/1 |
| 5,776,130 A | * | 7/1998 | Buysse et al. ................... 606/48 |
| 5,941,869 A | | 8/1999 | Patterson et al. |
| 6,039,733 A | | 3/2000 | Buysse et al. |
| 6,179,834 B1 | | 1/2001 | Buysse et al. |
| 6,743,239 B1 | | 6/2004 | Kuehn et al. |
| 6,997,931 B2 | | 2/2006 | Sauer et al. |
| 7,246,734 B2 | | 7/2007 | Shelton, IV |
| 7,766,910 B2 | * | 8/2010 | Hixson et al. ................... 606/51 |
| 2002/0062136 A1 | | 5/2002 | Hillstead |
| 2008/0009860 A1 | | 1/2008 | Odom |
| 2008/0125797 A1 | | 5/2008 | Kelleher |

FOREIGN PATENT DOCUMENTS

| | | |
|---|---|---|
| CA | 2104423 | 2/1994 |
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |

(Continued)

OTHER PUBLICATIONS

International Search Report EP10000259 dated Jun. 30, 2010.

(Continued)

*Primary Examiner* — Nicholas Lucchesi
*Assistant Examiner* — Rebecca E Eisenberg

(57) ABSTRACT

A forceps is provided. The forceps includes a housing having a shaft that extends therefrom. The bipolar forceps also includes a hydraulic mechanism that includes a fluid line and a plunger operatively coupled to the fluid line. The plunger is translatable within at least a portion of the shaft from a proximal position to a distal position. An end effector assembly is operatively connected to a distal end of the shaft and includes a pair of first and second jaw members biased in an open configuration. Each of the first and second jaw members configured to receive at least a portion of the plunger when a fluid is caused to flow within the fluid line such that the first and second jaw members move from an open position for positioning to a closed position for grasping tissue.

12 Claims, 4 Drawing Sheets

FOREIGN PATENT DOCUMENTS

| | | |
|---|---|---|
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 202007009317 | 8/2007 |
| DE | 19738457 | 1/2009 |
| EP | 1159926 | 12/2001 |
| EP | 1785097 | 5/2007 |
| EP | 1785098 | 5/2007 |
| EP | 1997438 | 12/2008 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 97/10764 | 3/1997 |
| WO | WO 03/101311 | 12/2003 |
| WO | WO2004028585 | 4/2004 |

OTHER PUBLICATIONS

U.S. Appl. No. 12/336,970, filed Dec. 17, 2008.
U.S. Appl. No. 12/399,614, filed Mar. 6, 2009.
U.S. Appl. No. 12/195,624, filed Aug. 21, 2008.
U.S. Appl. No. 12/367,791, filed Feb. 9, 2009.
U.S. Appl. No. 12/361,367, filed Jan. 28, 2009.
U.S. Appl. No. 12/361,375, filed Jan. 28, 2009.
U.S. Appl. No. 12/400,901, filed Mar. 10, 2009.
U.S. Appl. No. 12/176,679, filed Jul. 21, 2008.
U.S. Appl. No. 12/237,515, filed Sep. 25, 2008.
U.S. Appl. No. 12/204,976, filed Sep. 5, 2008.
U.S. Appl. No. 12/192,170, filed Aug. 15, 2008.
U.S. Appl. No. 12/233,157, filed Sep. 18, 2008.
U.S. Appl. No. 12/237,582, filed Sep. 25, 2008.
U.S. Appl. No. 12/210,598, filed Sep. 15, 2008.
U.S. Appl. No. 12/200,154, filed Aug. 28, 2008.
U.S. Appl. No. 12/211,205, filed Sep. 16, 2008.
U.S. Appl. No. 12/244,873, filed Oct. 3, 2008.
U.S. Appl. No. 12/246,553, filed Oct. 7, 2008.
U.S. Appl. No. 12/248,115, filed Oct. 9, 2008.
U.S. Appl. No. 12/353,474, filed Jan. 14, 2009.
U.S. Appl. No. 12/353,470, filed Jan. 14, 2009.
U.S. Appl. No. 12/352,942, filed Jan. 13, 2009.
U.S. Appl. No. 12/237,556, filed Sep. 25, 2008.
U.S. Appl. No. 12/411,542, filed Mar. 26, 2009.
U.S. Appl. No. 12/248,104, filed Oct. 9, 2008.
U.S. Appl. No. 12/254,123, filed Oct. 20, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/236,666, filed Sep. 24, 2008.
U.S. Appl. No. 12/192,189, filed Aug. 15, 2008.
U.S. Appl. No. 12/192,243, filed Aug. 15, 2008.
U.S. Appl. No. 12/331,643, filed Dec. 10, 2008.
U.S. Appl. No. 12/353,466, filed Jan. 14, 2009.
U.S. Appl. No. 12/363,086, filed Jan. 30, 2009.
U.S. Appl. No. 12/419,729, filed Apr. 7, 2009.

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With The LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the.LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgeiy" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009 .
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0.dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

APPARATUS, SYSTEM, AND METHOD FOR PERFORMING AN ELECTROSURGICAL PROCEDURE

BACKGROUND

1. Technical Field

The present disclosure relates to an apparatus, system, and method for performing an electrosurgical procedure. More particularly, the present disclosure relates to an apparatus, system, and method for performing an electrosurgical procedure that employs an electrosurgical apparatus that includes an end effector assembly configured for use with various size access ports.

2. Description of Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, seal, cut, desiccate, and/or fulgurate tissue As an alternative to open electrosurgical forceps for use with open surgical procedures, many modern surgeons use endoscopes and endoscopic electrosurgical apparatus (e.g., endoscopic forceps) or laparoscopic apparatus for remotely accessing organs through smaller, puncture-like incisions or natural orifices. As a direct result thereof patients tend to benefit from less scarring and reduced healing time. For example, the endoscopic forceps are inserted into the patient through one or more various types of cannulas or access ports (typically having an opening that ranges from about five millimeters to about twelve millimeters) that has been made with a trocar; as can be appreciated, smaller cannulas are usually preferred.

Endoscopic forceps that are configured for use with small cannulas (e.g., cannulas less than five millimeters) may present design challenges for a manufacturer of endoscopic instruments.

SUMMARY

As noted above, smaller cannulas or access ports are usually preferred during an endoscopic procedure. However, because of size constraints of the cannula or access port, endoscopic forceps that are configured for use with smaller cannulas may present design challenges for a manufacturer (e.g., designing an end effector assembly of an endoscopic forceps without compromising the integrity and/or functionality thereof).

Therefore, it may prove useful an endoscopic forceps that includes an end effector assembly configured for use with various types of cannulas or access ports including those that are less than five millimeters. With this purpose in mind, the present disclosure provides A forceps is provided. The forceps includes a housing having a shaft that extends therefrom. The bipolar forceps also includes a hydraulic mechanism that includes a fluid line and a plunger operatively coupled to the fluid line. The plunger is translatable within at least a portion of the shaft from a proximal position to a distal position. An end effector assembly is operatively connected to a distal end of the shaft and includes a pair of first and second jaw members biased in an open configuration. Each of the first and second jaw members configured to receive at least a portion of the plunger when a fluid is caused to flow within the fluid line such that the first and second jaw members move from an open position for positioning to a closed position for grasping tissue.

The present disclosure also provides a method for performing an electrosurgical procedure. The method includes the initial step of providing an electrosurgical instrument including a hydraulic mechanism that includes a fluid line and a plunger operatively coupled thereto. An end effector assembly includes a pair of first and second jaw members biased in an open configuration. The method also includes the steps of: positioning tissue between the pair of first and second jaw members; actuating the hydraulic mechanism to cause the first and second jaw members to move towards each other such that tissue is grasped therebetween; and applying electrosurgical energy to the jaw members such that a tissue seal may be effected therebetween.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful to provide an electrosurgical apparatus that is suitable for use with various access ports, including but not limited to those that are greater than and/or less than five millimeters. With this purpose in mind, the present disclosure includes an electrosurgical forceps that includes a hydraulic actuated end effector assembly having a pair of jaw members that operatively couple to a hydraulic mechanism that moves the jaw members from an open position for positioning tissue to a closed position for grasping tissue and causing a tissue effect therebetween. The hydraulic actuated end effector assembly of the present disclosure provides the needed force required for fusing or sealing tissue when the electrosurgical forceps is one of in either a non-articulated or articulated configuration.

Figure 1:
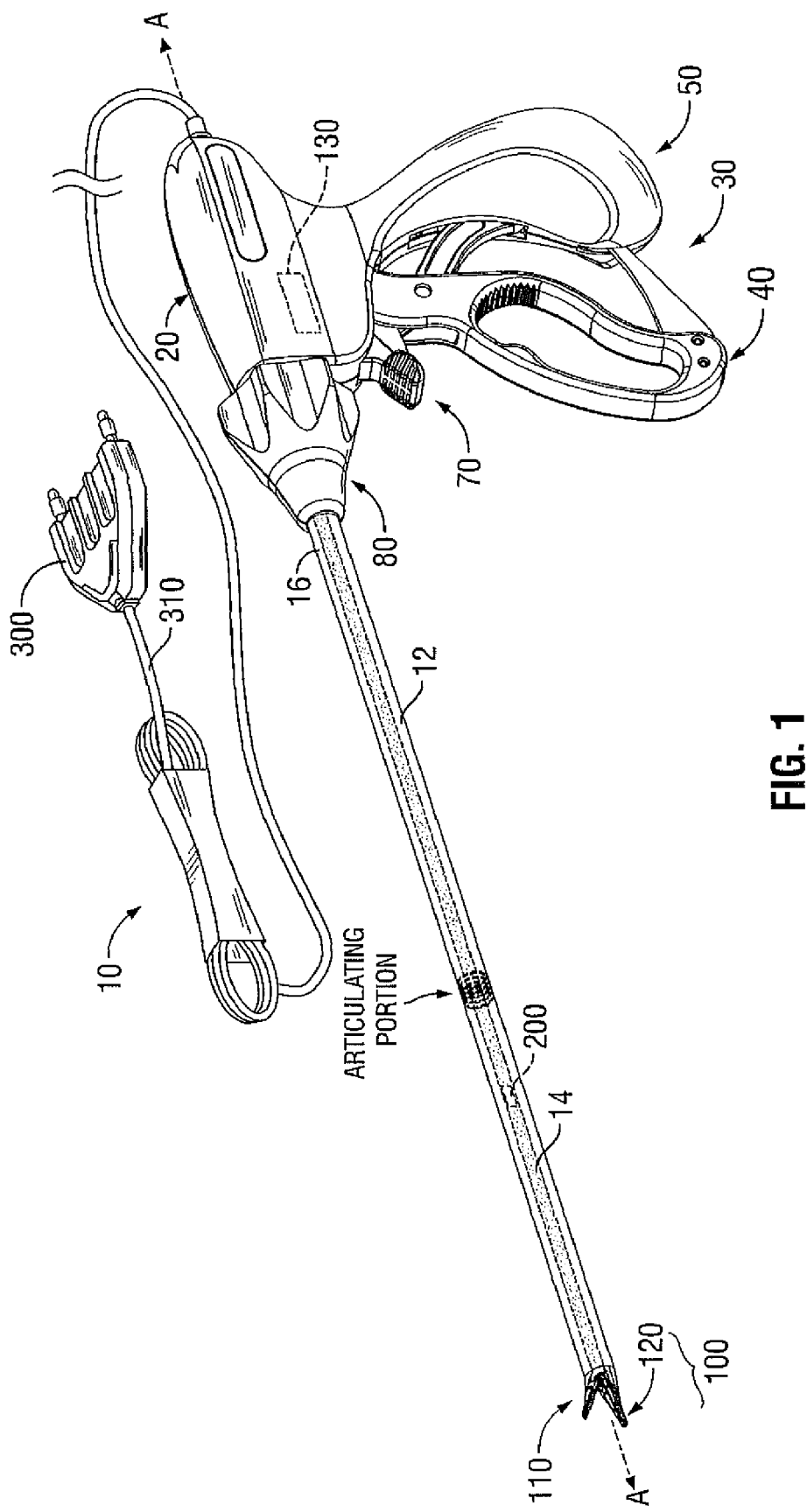
FIG. 1 is a perspective view of a bipolar forceps including an end effector assembly and electrosurgical generator according to an embodiment of the present disclosure.
Figure 2:
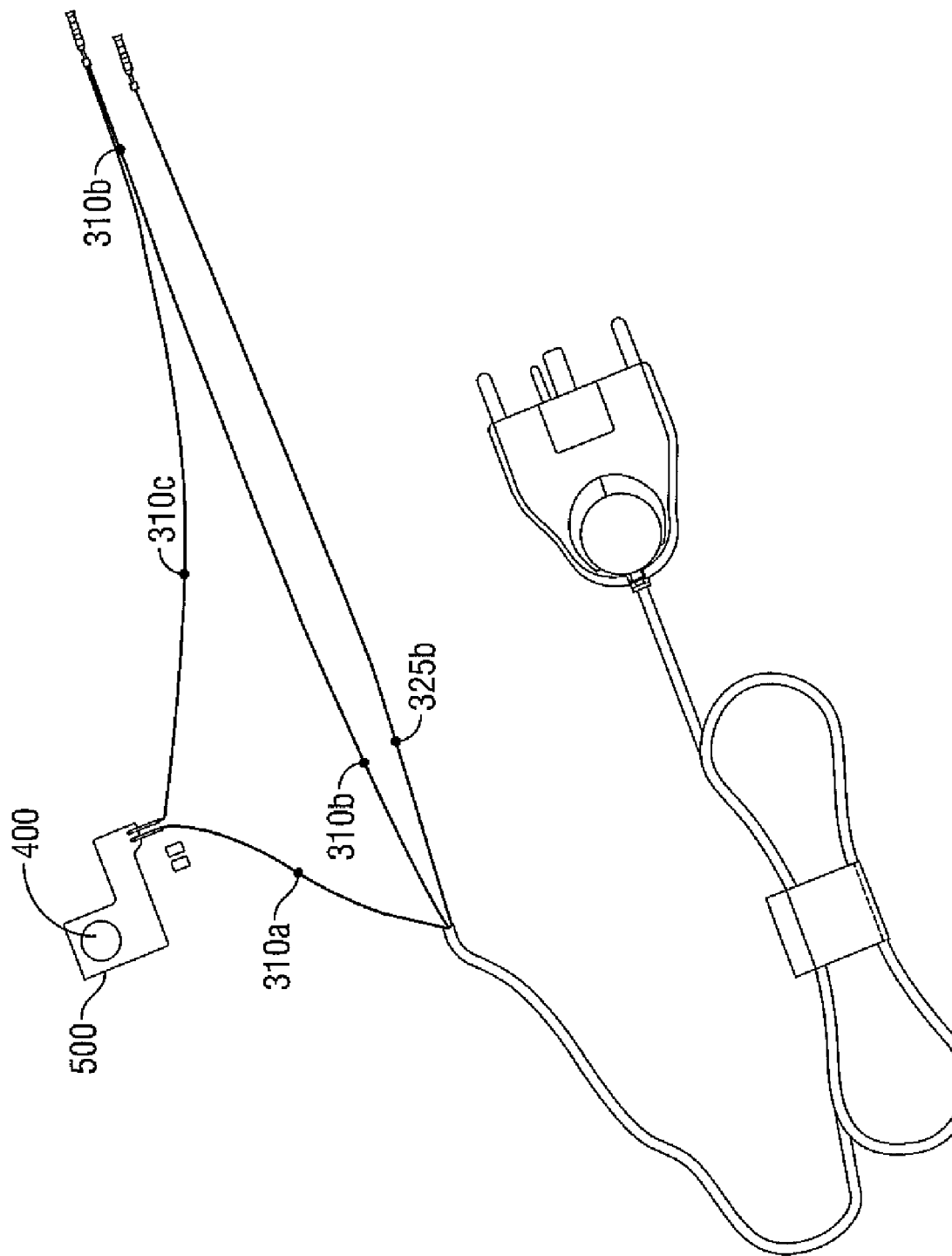
FIG. 2 is a schematic representation of an electrical configuration for connecting the bipolar forceps to the electrosurgical generator depicted in FIG. 1.

With reference to FIG. 1 an illustrative embodiment of an electrosurgical apparatus (e.g., bipolar forceps 10) for performing an electrosurgical procedure is shown. Bipolar forceps 10 is operatively and selectively coupled to an electrosurgical generator (generator 200, see FIG. 2 for example) for performing an electrosurgical procedure. As noted above, an electrosurgical procedure may include sealing, cutting, cauterizing coagulating, desiccating, and fulgurating tissue all of which may employ RF energy. Generator 200 may be configured for monopolar and/or bipolar modes of operation. Generator 200 may include or is in operative communication with a system (system 400, see FIG. 2) that may include one or more processors in operative communication with one or more control modules that are executable on the processor. A control module (not explicitly shown) instructs one or more modules to transmit electrosurgical energy, which may be in the form of a wave or signal/pulse, via one or more cables (e.g., a cable 310) to one or both of the seal plates 118, 128. For a more detailed description of the generator 200 and/or system 300 reference is made to commonly owned U.S. application Ser. No. 10/427,832.

With reference again to FIG. 1, bipolar forceps 10 is shown for use with various electrosurgical procedures and generally includes a housing 20, a handle assembly 30, a rotating assembly 80, a trigger assembly 70, a drive assembly 130, and an end effector assembly 100 that operatively connects to the drive assembly 130. Drive assembly 130 is in operative communication with a hydraulic mechanism 200 for imparting movement of one or both of a pair of jaw members 110, 120 of end effector assembly 100. End effector assembly 100 includes opposing jaw members 110 and 120 (FIG. 1) that mutually cooperate to grasp, seal and, in some cases, divide large tubular vessels and large vascular tissues. Although the majority of the figure drawings depict a bipolar forceps 10 for use in connection with laparoscopic surgical procedures, the present disclosure may be used for more traditional open surgical procedures or endoscopic procedures. For the purposes herein, the forceps 10 is described in terms of a laparoscopic instrument; however, an open version or endoscopic version of the forceps may also include the same or similar operating components and features as described below.

Forceps 10 includes a shaft 12, as described in greater detail below with reference to FIGS. 3A-3B that has a distal end 14 configured to mechanically engage the end effector assembly 100 and a proximal end 16 that mechanically engages the housing 20. In the drawings and in the descriptions that follow, the term "proximal," as is traditional, will refer to the end of the forceps 10 which is closer to the user, while the term "distal" will refer to the end that is farther from the user.

With continued reference to FIG. 1, handle assembly 30 includes a fixed handle 50 and a movable handle 40. Fixed handle 50 is integrally associated with housing 20 and handle 40 is movable relative to fixed handle 50. Fixed handle 50 may include one or more ergonomic enhancing elements to facilitate handling, e.g., scallops, protuberances, elastomeric material, etc.

Movable handle 40 of handle assembly 30 is ultimately connected to drive assembly 130, which together mechanically cooperate to impart movement of hydraulic mechanism 200. Movement of hydraulic mechanism 200 causes jaw members 110 and 120 to move from an open position, wherein the jaw members 110 and 120 are disposed in spaced relation relative to one another, to a clamping or closed position, wherein the jaw members 110 and 120 cooperate to grasp tissue therebetween.

Rotating assembly 80 is operatively associated with the housing 20 and is rotatable approximately 180 degrees about a longitudinal axis "A-A" defined through shaft 12 (see FIG. 1).

Forceps 10 also includes an electrosurgical cable 310 that connects the forceps 10 to a source of electrosurgical energy, e.g., generator 200. Cable 310 is internally divided into cable leads 310a, 310b, 310c, and 325b (see FIG. 2) that are designed to transmit electrical potentials through their respective feed paths through the forceps 10 to the end effector assembly 100. More particularly, cable feed 325b connects through the forceps housing 20 and through the rotating assembly to jaw member 120. Lead 310a connects to one side of a switch (not shown) and lead 310c connects to the opposite side of the switch such that upon activation of the switch energy is transmitted from lead 310a to 310c. Lead 310c is spliced with lead 310b that connects through the rotating assembly to jaw member 110.

For a more detailed description of handle assembly 30, movable handle 40, rotating assembly 80, electrosurgical cable 310 (including line-feed configurations and/or connections), and drive assembly 130 reference is made to commonly owned U.S. application Ser. No. 10/369,894.

Figure 3A:
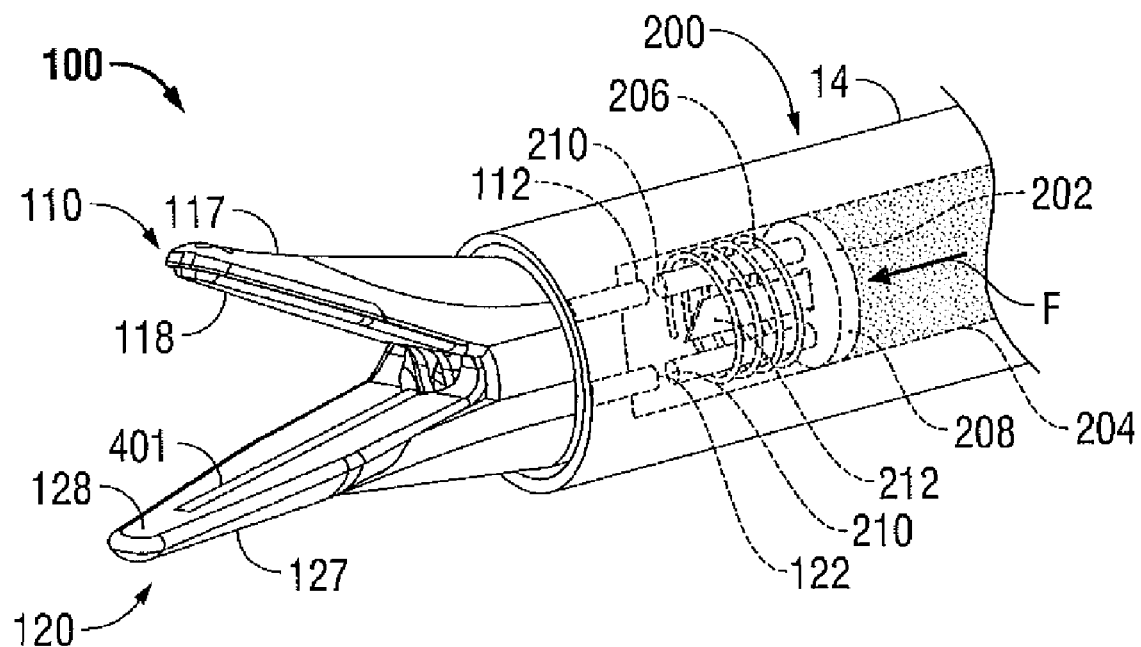
FIG. 3A is an enlarged, front perspective view of the end effector assembly of FIG. 1 shown in an open configuration.

Turning now to FIG. 3A, shaft 12 includes distal end 14 operatively connected to end effector assembly 100 and hydraulic mechanism 200. Shaft 12 is configured to house drive assembly 130 and hydraulic mechanism 200 or portions thereof. At distal end 14 of shaft 12, jaw members 110 and 120, or portions thereof, are attached to an inner surface of shaft 12 via any suitable attaching means including but not limited to staking, welding, riveting, molding or overmolding.

Distal end 14 of shaft 12 is adapted to provide reciprocation of one or more plungers 202 and/or a knife blade 212 of hydraulic mechanism 200. Additionally, distal end 14 is configured to allow jaw members 110 and 120 to pivot from an opened to closed configuration, during translation of the plungers 202 therein (as explained in more detail below). A seal or sealing structure (not explicitly shown), such as a gasket, may be operatively disposed at or near the distal end 14 of shaft 12 and configured to provide a substantially fluid tight seal between end effector assembly 100 and plunger 202.

With continued reference to FIGS. 3A, hydraulic mechanism 200 is shown. Hydraulic mechanism 200 includes a fluid line 204 that is in fluid communication with one or more of the plungers 202. Hydraulic mechanism 200 (and components associated therewith) may be made from any suitable biocompatible material.

Fluid line 204 includes one or more suitable bio-compatible fluids "F" therein. Fluids "F" suitable for use with fluid line 204 of hydraulic mechanism 200 may include synthetic compounds, mineral oil, water, and water-based mixtures. Fluid line 204, and/or fluid "F" contained therein, is in operative communication with the drive assembly 130, plunger 202, and/or distal end 14 of shaft 12 by way of one or more suitable internal connections and/or components. Internal mechanically cooperating components associated with the drive assembly 130 and/or fluid lines 204 impart movement of the jaw members 110, 120 of end effector assembly 100. Suitable components include any number of vacuum boosters or servos, cylinders, pistons, drums, gears, links, valves, springs, and/or rods such that forceps 10 may function as intended. When a force is applied to one or more components (e.g., piston) associated with the hydraulic mechanism 200, pressure in the hydraulic mechanism increases, forcing the fluid "F" through the fluid line 204 to the one or more plungers 202.

Plunger 202 is in operative communication with the fluid line 204 and/or fluid "F" such that the plunger 204 is selectively translatable from a proximal position to a distal position (e.g., engaged with one or both of the jaw members 110, 120) within shaft 12. In the embodiments illustrated in FIGS.

3A and 3B, plunger 202 is shown operatively disposed at a distal end 14 of shaft 12 and adjacent to a proximal end of each of the jaw members 110, 120. Plunger 202 includes a proximal end that defines a base 208 that includes one or more prongs 210 (two prongs 210 are shown) extending therefrom and configured to engage one or more corresponding apertures 112, 122 located at proximal ends of one or both of the jaw members 110, 120, respectively. Prongs 210 extend longitudinally from the base 208 of plunger 202 and are disposed in a substantially parallel relation to one another. One or more springs 206 bias plunger 202 in a proximal orientation. As shown in the illustrated FIGS., spring 206 is operatively disposed on plunger 202. However, in some embodiments, spring 206 may be operatively coupled to the proximal ends of the jaw members 110, 120 and/or end effector assembly 100.

Figure 3B:
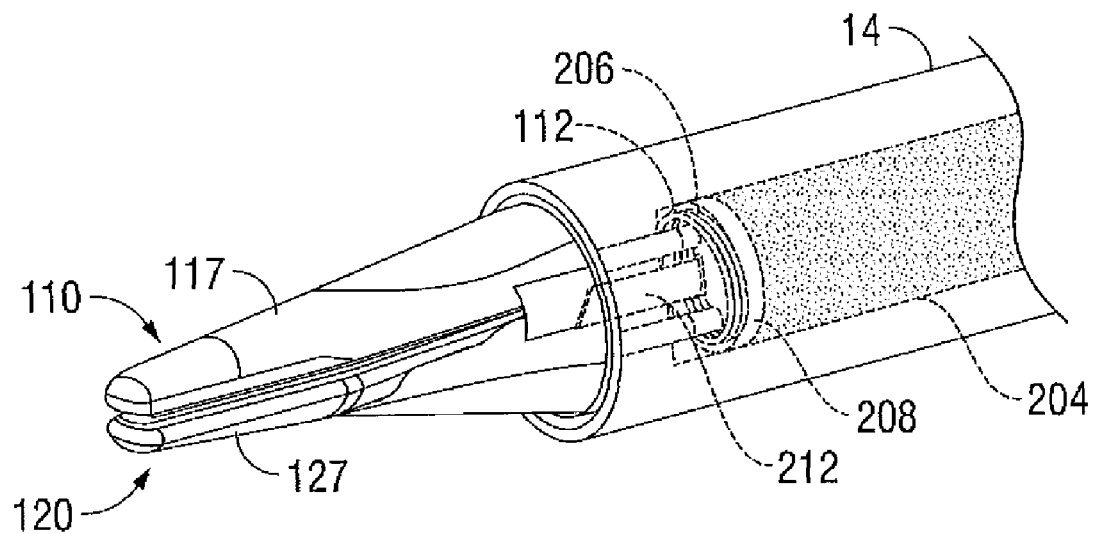
FIG. 3B is an enlarged, front perspective view of the end effector assembly of FIG. 1 shown in a closed configuration.
Figure 4:
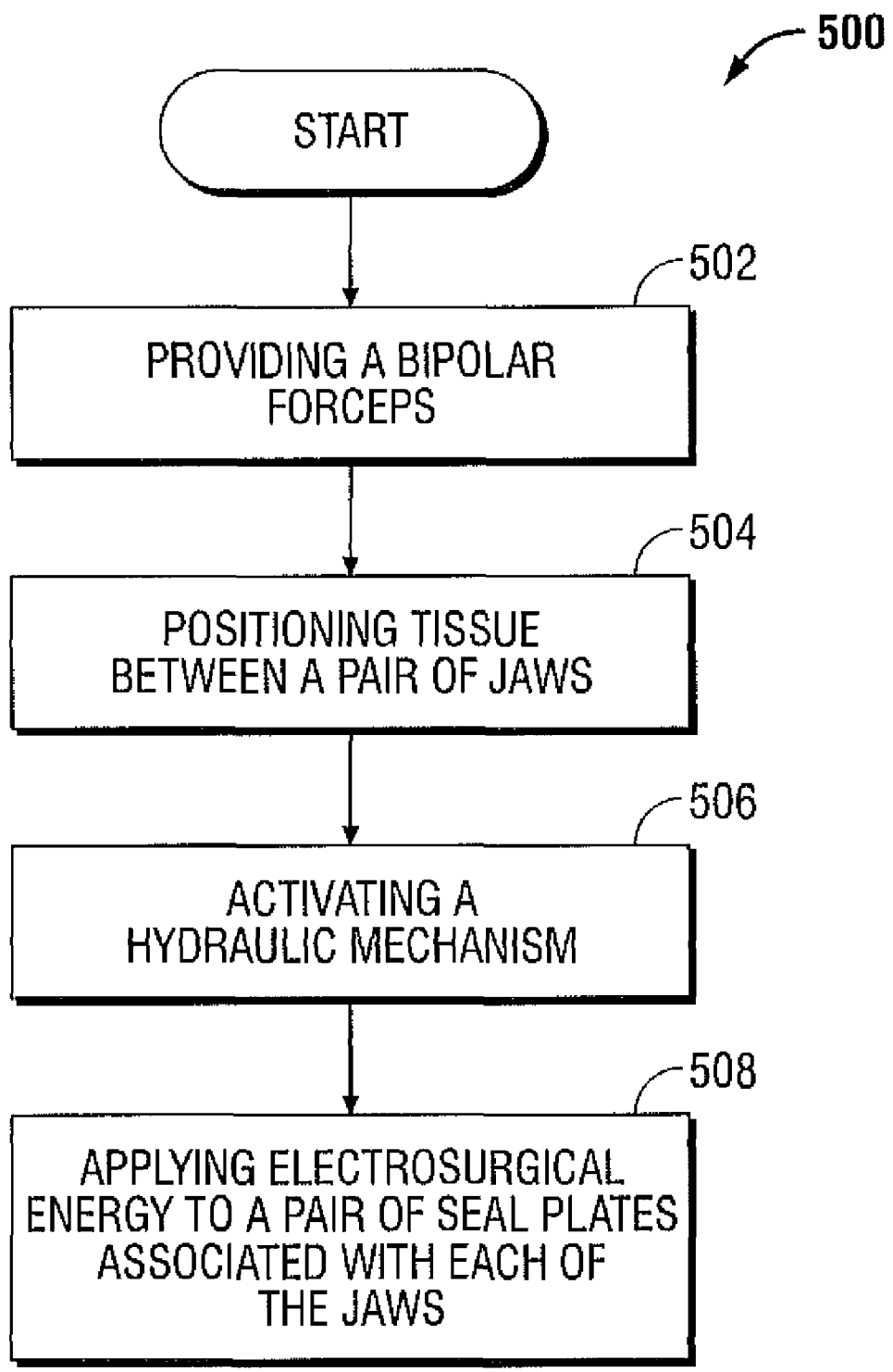
FIG. 4 is a flowchart illustrating a method for performing an electrosurgical procedure in accordance with the present disclosure.

In the embodiments illustrated in FIGS. 3A and 3B, plunger 202 includes a plunger 212 that operatively couples to a knife blade or cutter 212 that is translatable within a knife channel 401 operatively disposed on one or both of the jaw members 110, 120. Plunger 212 is movable relative to the plunger 202 from a proximal position to a distal position and is configured to translate the knife to transect or sever tissue after a tissue effect has been achieved.

End effector assembly 100 includes opposing jaw members 110 and 120 that are fixedly attached shaft 12. Jaw members 110, 120 may be operatively and pivotably coupled to each other and located adjacent the distal end 14 of shaft 12.

Jaw member 110 includes an insulative jaw housing 117 and an electrically conductive seal plate 118 (hereinafter seal plate 118). The insulator 117 is configured to securely engage the electrically conductive seal plate 118. This may be accomplished by stamping, by overmolding, by overmolding a stamped electrically conductive sealing plate and/or by overmolding a metal injection molded seal plate. All of these manufacturing techniques produce an electrode having a seal plate 118 that is substantially surrounded by the insulating substrate. Within the purview of the present disclosure, jaw member 110 may include a jaw housing 117 that is integrally formed with a seal plate 118.

Jaw member 120 includes a similar structure having an outer insulative housing 127 that may be overmolded to capture seal plate 128.

Each of the jaw members 110, 120 is configured to engage a respective prong 210 of plunger 202 such that each of the jaw members 110, 120 are movable from an open position, wherein the jaw members 110 and 120 are disposed in spaced relation relative to one another, to a closed position, wherein the jaw members 110 and 120 cooperate to grasp tissue therebetween. With this purpose in mind, each of the jaw members 110, 120 include respective apertures 112, 122 located at proximal ends thereof. Apertures 112, 122 extend within each of the jaws 110, 120, respectively, a distance that allows the prongs 210 of plunger 202 to translate therein such that jaw members 110, 120 are caused to move from the open to the closed position. A substantially fluid tight seal structure may be operatively disposed with the apertures 112, 122 and configured to maintain a constant pressure within the fluid line 204. As noted above, a portion of the proximal ends of each of the jaw members 110, 120 may include structure that engages or contacts the spring 206.

In use, prior to sealing tissue, jaw members 110 and 120 are initially biased in an open configuration (FIG. 3A). A user may position tissue between the jaw members 110, 120. When tissue is properly positioned between the jaw members 110, 120, a user may activate the hydraulic mechanism 200, for example, by way of movable handle 40. When the movable handle 40 is moved proximally, leverage (provided by linkage system, not explicitly shown) may multiply the force (provided by the movable handle 40 moving proximally) to one or more components associated with the hydraulic mechanism 200 (e.g. piston, not explicitly shown). The applied force to the piston increases pressure in the fluid line 204 of the hydraulic mechanism 200, which causes fluid "F" to flow through the fluid lines 204 to the plunger 202. This fluid flow causes the plunger 202 to translate distally within the shaft 12 and/or fluid line 204. This translation of plunger 202 causes the prongs 210 to engage the apertures 112, 122 of proximal end jaw members 110, 120, respectively, which, in turn, cause the jaw members 110, 120 to move from the open position to the closed position, wherein the jaw members 110, 120 cooperate to grasp tissue.

Once tissue has been grasped (FIG. 3B), a user may activate generator 200, for example, via button 60, such that a desired tissue effect may be achieved (e.g., a tissue seal). After the desired tissue effect has been achieved, a user may release the moveable handle 40, which, in turn, causes the movable handle 40 to move distally. This distal movement of movable handle 40 releases some, if not all, of the pressure built up in the fluid line 204 such that the plunger 202 under the biasing force of the spring 206 is caused to move proximally and out of engagement with the apertures 112, 122 of jaw members 110, 120, respectively, and, thus, back to their initial open position.

In some embodiments, after a desired tissue effect has been achieved, a user may also activate the knife blade 212 to transect or sever the effected tissue. More particularly, while tissue is grasped between the jaw members 110, 120 and the plunger is in a distal position, a user may, for example, apply additional pressure to the movable handle 40 such that the plunger 212 is caused to translate distally. In this instance, plunger 202 is maintained in a fixed position via the proximal end of the jaw members 110, 120 and the plunger 212 is free to translate within the knife channel 400 such that tissue may be severed.

From the foregoing and with reference to the various figure drawings, those skilled in the art will appreciate that certain modifications can also be made to the present disclosure without departing from the scope of the same. For example, a pneumatic mechanism may be employed instead of a hydraulic mechanism 200. In this instance, the pneumatic mechanism, and operative components associated therewith, would mutually cooperate to function in a manner as described hereinabove with reference to the hydraulic mechanism 200.

The present disclosure also provides a method 500 for performing an electrosurgical procedure. As illustrated in FIG. 5, at step 502 a bipolar forceps is provided. At step 504, tissue is positioned between the pair of first and second jaw members such that a tissue seal may be effected. At step 506, the drive assembly is actuated to move the actuation tube causing the cam pin to cam the first and second jaw members to pivot about the living hinge and cam towards each other such that tissue is grasped therebetween. And at step 508, electrosurgical energy is applied to the jaw members such that a tissue seal may be effected therebetween.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps adapted to connect to a source of electrosurgical energy for performing an electrosurgical procedure comprising:
    a housing having a shaft that extends therefrom that defines a longitudinal axis therethrough;
    a hydraulic mechanism that includes a fluid line and a plunger operatively coupled to the fluid line, the plunger translatable within at least a portion of the shaft; and
    an end effector assembly operatively connected to a distal end of the shaft having a pair of first and second jaw members biased in an open configuration, each of the first and second jaw members including at least one aperture at a proximal end thereof configured to receive at least a portion of the plunger when the fluid is caused to flow within the fluid line such that the first and second jaw members move from an open position wherein the jaw members are disposed in spaced relation relative to one another, to a clamping wherein the jaw members cooperate to grasp tissue therebetween.

2. A bipolar forceps according to claim 1, wherein each of the first and second jaw members are pivotable about a pivot pin located at the distal end of the shaft.

3. A bipolar forceps according to claim 1, wherein the plunger includes at least two prongs extending from a proximal portion thereof configured to engage the at least one aperture associated with each of the first and second jaw members.

4. A bipolar forceps according to claim 1, wherein the plunger includes a biasing member that biases the plunger proximally in an uncompressed state.

5. A bipolar forceps according to claim 1, wherein the plunger includes a knife blade operatively coupled thereto configured for translatable motion within a knife slot defined within at least one of the first and second jaw members.

6. A bipolar forceps according to claim 1, wherein the first and second jaw members are biased via a spring.

7. A method for performing an electrosurgical procedure, the method comprising:
    providing an electrosurgical instrument including:
        a hydraulic mechanism that includes a fluid line and a plunger operatively coupled to the fluid line; and
        an end effector assembly having a pair of first and second jaw members biased in an open configuration, wherein the first and second jaw members each include at least one aperture located at a proximal end thereof, the at least one aperture on each of the jaw members configured to receive at least a portion of the plunger;
    positioning tissue between the pair of first and second jaw members;
    actuating the hydraulic mechanism to cause the first and second jaw members to move towards each other such that tissue is grasped therebetween; and
    applying electrosurgical energy to the jaw members to effectively seal tissue therebetween.

8. A method according to claim 7, further comprising the step of cutting the tissue with a knife blade associated with the plunger.

9. A method according to claim 7, wherein the step of providing further includes providing the plunger with at least two prongs extending from a proximal portion thereof configured to engage the at least one aperture associated with each of the first and second jaw members.

10. A method according to claim 7, wherein the step of providing further includes providing the plunger with a biasing member that biases the plunger proximally in an uncompressed state.

11. A method according to claim 7, wherein the step of providing further includes providing the plunger with a knife blade operatively coupled thereto and configured for translatable motion within a knife slot defined within at least one of the first and second jaw members.

12. A method according to claim 7, wherein the step of providing further includes biasing the first and second jaw members via a spring.

* * * * *